United States Patent [19]

Nowinski et al.

[11] Patent Number: 4,711,840

[45] Date of Patent: * Dec. 8, 1987

[54] POLYMERIZATION-INDUCED SEPARATION IMMUNOASSAYS

[75] Inventors: Robert C. Nowinski; Allan S. Hoffman, both of King County, Wash.

[73] Assignee: Genetic Systems Corporation, Seattle, Wash.

[*] Notice: The portion of the term of this patent subsequent to Apr. 16, 2002 has been disclaimed.

[21] Appl. No.: 668,247

[22] Filed: Nov. 7, 1984

Related U.S. Application Data

[63] Continuation-in-part of Ser. No. 574,558, Jan. 27, 1984, which is a continuation-in-part of Ser. No. 550,929, Nov. 10, 1983, Pat. No. 4,511,478.

[51] Int. Cl.$^4$ ................. G01N 33/537; C12Q 1/68
[52] U.S. Cl. ........................... 435/7; 435/6; 436/501; 436/504; 436/513; 436/531; 436/533; 436/534; 436/538; 436/539; 436/548; 436/800; 525/904; 526/238.1; 527/202

[58] Field of Search ............ 435/7, 6; 436/513, 531, 436/533, 534, 800, 501, 504, 538, 539, 548; 526/238.1; 525/904; 527/202

[56] References Cited

U.S. PATENT DOCUMENTS

| | | | |
|---|---|---|---|
| 2,853,457 | 9/1958 | Gates et al. | 524/704 |
| 3,969,287 | 7/1976 | Jaworek et al. | 435/176 |
| 4,061,466 | 12/1977 | Sjohölm et al. | 436/535 |
| 4,469,796 | 9/1984 | Axén et al. | 436/518 |
| 4,609,707 | 9/1986 | Nowinski | 436/541 |

Primary Examiner—Esther M. Kepplinger
Assistant Examiner—Robert Benson
Attorney, Agent, or Firm—Bertram I. Rowland

[57] ABSTRACT

Immunoassay methods and compositions are disclosed for the detection of one or more analytes in fluid samples. The disclosure provides conjugates of analytes or reactants with polymerizable organic monomers. Specific binding reactions between reactants are detected by means of reporter/reactant conjugates. Free and specifically-bound reporter/reactant conjugates are separated by a polymerization reaction which renders the polymerized monomers insoluble.

15 Claims, 5 Drawing Figures

POLYMERIZATION-INDUCED SEPARATION IMMUNOASSAYS

CROSS-REFERENCE TO RELATED APPLICATION

This application is a continuation-in-part of U.S. patent application Ser. No. 574,558, filed on Jan. 27, 1984, which is a continuation-in-part of U.S. patent application Ser. No. 550,929, filed on Nov. 10, 1983 now U.S. Pat. No. 4,511,478.

DESCRIPTION a. Technical Field

The present invention relates generally to immunoassay methods and more particularly to an immunoassay in which a polymerization reaction is used to effect a separation of the specific reactants.

b. Background Art

1. Immunoassays

Immunoassays have found widespread application in the field of clinical diagnostics for the detection and measurement of drugs, vitamins, hormones, proteins, metabolites, microorganisms, and other substances of interest (analytes) in biological and nonbiological fluids. Typically, these analytes occur in micromolar ($10^{-6}$M) or less concentration.

Immunoassays generally incorporate antibodies and antigens as reactants, at least one of which is labeled with a signal producing compound (e.g. radioisotope, fluorophore, etc.). Following mixture with the sample and incubation, specific antibody/antigen reactions occur (specific binding). The reaction mixture is subsequently interrogated to detect free and specifically-bound labeled reactant, enabling a measurement of the analyte in the sample.

Immunoassays can be divided into two general categories, homogeneous and heterogeneous. In a homogeneous immunoassay, the signal emitted by the specifically-bound labeled reactant is different from the signal emitted by the free labeled reactant. Hence, bound and free can be distinguished without physical separation.

The archetypal homogeneous immunoassay is the enzyme-multiplied immunoassay technique (EMIT), which is disclosed in U.S. Pat. No. 3,817,837. In this technology, analyte present in patient sample and analyte/enzyme conjugate compete for a limited amount of anti-analyte antibody. Specific binding of antibody to the conjugate modulates its enzymatic activity. Hence, the amount of enzyme activity is proportional to the amount of analyte in the sample. Homogeneous immunoassays have the advantage of being rapid, easy to perform, and readily amenable to automation. Their principal disadvantages are that they are relatively prone to interferences, are generally limited in sensitivity to approximately $10^{-9}$M.

In a heterogeneous immunoassay, the signal emitted by the bound labeled reactant is indistinguishable from the signal emitted by the free labeled reactant. Therefore, a separation step is required to distinguish between the two.

Typical heterogeneous immunoassays include the radioimmunoassay (RIA) and the enzyme-linked immunosorbent assay (ELISA). In the RIA, radiolabeled analyte and analyte present in patient sample compete for a limited amount of immobilized (solid phase) anti-analyte antibody. The solid phase is washed to remove unbound labeled analyte and either the bound or the free fraction is analyzed for the presence of labeled reactant. ELISA assays are performed analogously. In this case, though, the signal is an enzyme instead of a radioisotope. Heterogeneous immunoassays typically employ at least one reagent immobilized on a solid phase. Since the kinetics of reaction between an immobilized antibody (or antigen) and its binding site tend to be slower than the kinetics of the same reaction occurring in solution, long incubation times are frequently required. When the multiple wash steps often needed are considered, it can be appreciated that heterogeneous assays tend to be time-consuming and labor-intensive. However, they are in general more sensitive than homogeneous assays and less prone to interferences, since interfering substances can be removed in the wash steps.

Solids used to immobilize reactants in immunoassays have included controlled pore glass and preformed polymers such as polyvinyls, polyacrylamide, polydextrans and polystyrene.

Numerous separation methods are known in the art and have been used in heterogeneous immunoassays. These include centrifugation, filtration, affinity chromatography, gel permeation chromatography, etc.

The homogeneous immunoassay methods of the prior art are generally prone to interferences, of limited sensitivity and have a limited range of antigen sizes. The heterogeneous immunoassays of the prior art, while increasing the sensitivity and minimizing interferences, tend to be time consuming and labor intensive. These difficulties generally arise from the added step of physical separation and the need for numerous washes to decrease background interference.

There is a need in the art for an immunoassay method which is sensitive to sub-micromolar concentrations of analyte; which has fast reaction kinetics; and which minimizes the number of manipulations necessary to achieve a result.

2. Polymer Chemistry

A reaction fundamental to polymer chemistry is the initiation of end-to-end covalent linkages between soluble organic monomers leading to the formation of larger polymeric molecular structures (polymers). Synthetic polymers can be formed from a single monomeric species (homopolymer) or from a mixture of different monomers (copolymer). Linear, branched, cross-linked structures are possible. By varying the chemical composition or ratios of the monomers, it is possible to form either soluble or insoluble polymers which comprise a broad range of chemical and physical structures. For example, water-soluble monomers (such as acrylamide) can be copolymerized to form water-soluble homopolymers. They can also be copolymerized with less water-soluble monomers (such as N-alkyl or N,N-dialkyl acrylamides) or with cross-linking monomers (such as N,N'-methylenebisacrylamide to form water-soluble copolymer structures. Some water-soluble monomers (such as hydroxyethyl methacrylate or acrylonitrile) can be homopolymerized to form water-insoluble homopolymers.

In the fields of biochemistry and immunology, water-insoluble polymers (such as polysaccharides or polyacrylics, sometimes cross-linked) have been commonly used as solid phase supports with passively absorbed, physically entrapped, or covalently-linked proteins in affinity chromatography, enzyme immobilization, and immunoassay. See, for example, U.S. Pat. Nos.

3,957,741; 4,257,884; 4,195,129; 4,225,784; 4,181,633; 4,401,765; and 4,166,105.

To date, the documented coupling of a polypeptide to a polymer has occurred under circumstances in which the polypeptide was provided in soluble form and the polymer was provided as a preformed soluble or preformed insoluble material. While these polymers are of utility in providing a surface upon which selective biochemical or immunological reactions can occur, the polymers are of limited value in that the spacing, steric accessibility, and number of polypeptides bound per unit length of polymer cannot be precisely or reproducibly controlled. Lot-to-lot variation is commonly encountered during the manufacture of such solid phase polymer/reactant matrices. In certain end-use applications where reproducibility and standardization are essential (e.g. immunoassays), this variation in composition of the solid-phase polymer/reactant matrices presents a critical problem. Consequently, there is a need in the art for a method to specifically tailor or molecularly engineer polymer compounds incorporating controlled quantities of reactants.

DISCLOSURE OF THE INVENTION

The present invention provides immunoassay methods for determining the presence of an analyte in a fluid sample suspected of containing said analyte comprising contacting said fluid sample with a monomer/reactant conjugate in order to form a monomer/reactant conjugate-analyte complex and providing a reporter for said monomer/reactant conjugate-analyte complex, separating said reporter-labeled complex by initiating polymerization of the monomer/reactant conjugate-analyte complex and detecting the incorporation of reporter into said polymerized complex.

Another aspect of the invention provides immunoassay methods utilizing monomer/analyte conjugates for competitive immunoassays.

Another aspect of the invention provides an immunoassay method for simultaneously measuring two or more analytes in a fluid sample.

A further aspect of the invention provides monomer/reactant and monomer/analyte conjugates for use in the immunoassays of the present invention.

A novel feature of this immunoassay is the use of reactant (antibody or antigen) that is covalently linked with a polymerizable organic monomer. Following mixture and reaction of the immunoassay components, the monomer/reactant conjugate and its specific binding complement (i.e., its appropriate antigen or antibody counterpart bound through specific antibody/antigen interactions) can be rapidly and conveniently separated from solution by initiating a polymerization reaction. In contrast to the monomer/reactant conjugate and its specifically bound complement, other components of the immunoassay remain in free solution. Thus, this method provides an effective single-step step separation of specifically bound and free reactants.

The polymerization-induced separation immunoassays of the instant invention are believed to offer several advantages over prior art homogeneous and heterogeneous immunoassay methods. Because of the separation achieved by polymerization of the monomer/reactant conjugate, the immunoassay of this invention can achieve the sensitivity typical of state-of-the-art heterogeneous techniques combined with ease of performance of homogeneous techniques.

The immunoassays of this invention can typically be performed in less time than traditional heterogeneous assays because binding reactions which would normally occur on a solid phase can be made to occur in solution instead. Also, the need for extensive washing of the solid phase can be eliminated.

Sandwich immunoassay typically require elution of the specifically bound labeled reactant from the solid phase prior to measurement. This adds an extra step and makes even longer and more cumbersome an already long and tedious process. The immunoassay of this invention can be performed without the elution of the bound labeled reactant from the polymer, thus simplifying performance.

BEST MODE FOR CARRYING OUT THE INVENTION

Figure 1:
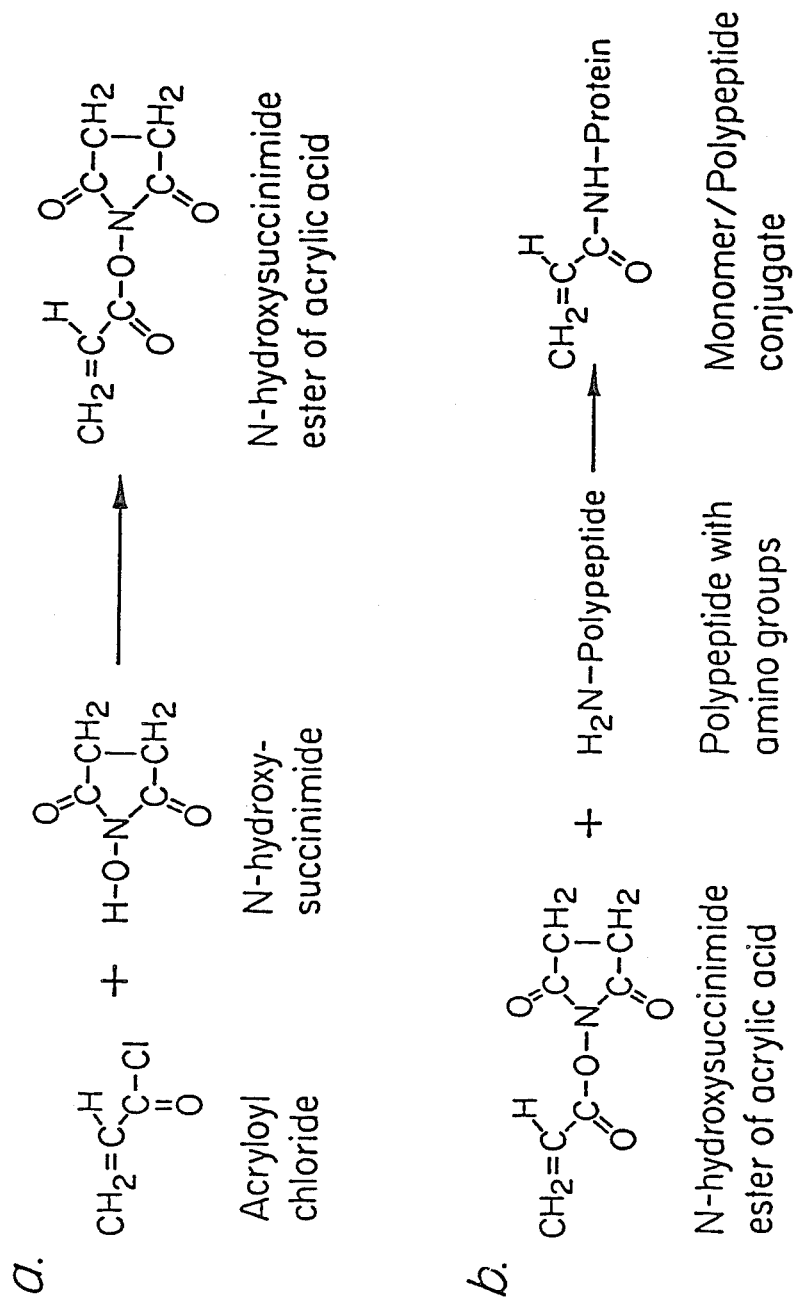
FIG. 1 is a diagrammatic representation of the synthesis of an activated acrylic acid monomer and a conjugation involving this monomer and, for example, amino groups on a reactant of the present invention.

Co-pending U.S. patent application Ser. No. 550,929 filed on Nov. 10, 1983 now U.S. Pat. No. 4,511,478, which is herein incorporated by reference, discloses methods and compounds for the selective removal of substances from solution by the de novo synthesis of organic polymers integrally containing a binding partner for the substance to be removed. U.S. Ser. No. 574,558, filed on Jan. 27, 1984, is directed toward an application of the technology to immunoassays, in which the binding partners are antigen and antibody reactants. The present invention is directed toward immunoassays based on this technology wherein two or more analytes can bae measured simultaneously by employing the corresponding number of reporter/reactant conjugates, each reporter being detectably different.

The methods of this invention for the immunoassay of analytes in biological fluids utilize conjugates of reactants with monomers or signal-producing compounds (monomer/reactant or reporter/reactant conjugates). Separation of free from specifically bound reporter/reactant is effected by a polymerization reaction. Detection of polymer-incorporated signal can be accomplished by a variety of methods, including flow microfluorimetry and filtration.

Although the following discussion pertains primarily to the immunoassay of analytes in biological fluids, it will be appreciated that there are numerous disciplines which require the assay of fluid samples for the presesnce or amount of organic substances. These disciplines include for example food preparation and environmental quality control.

For the purposes of this disclosure, the following terms are defined:

Analyte is the substance or group of substances the presence or amount of which it is desired to determine.

Biological fluids are blood, blood serum, blood plasma, urine, feces, cerebrospinal fluid, saliva, sputum, cell and tissue derived extracts, etc in which the analyte is suspected of being contained.

Reactants are naturally occurring or synthetic substances, typically antigens and antibodies, which are capable of recognizing and specifically binding to each other.

Antigen as used herein includes molecules which themselves may induce antibodies as well as small molecules which are not capable of eliciting antibody production unless they are coupled to a carrier (e.g. haptens).

Epitope is any antigenic determinant.

Monomer is any soluble organic compound which is capable of forming end-to-end covalent linkages (i.e. polymerizing) under the appropriate conditions.

Reporter is any substance which is capable of producing a detectable signal either alone or in combination with other reagents, such as, e.g., radioisotopes, fluorophores, chromophores, luminescent compounds, etc.

The immunoassays of the present invention can be performed in any of several configurations. These can include competitive, sandwich and noncompetitive immunoassay configurations. In every case the analyte of interest can be either an antigen or an antibody. In every case, either reactant (i.e, antigen or antibody) can be conjugated to either labeled substance i.e., monomer or reporter). The various possible configurations in which immunoassays can be performed are reviewed extensively in *Enzyme-Immunoassay*, E. T. Maggio (Ed.) CRC Press, Boca Raton, Fla. (1980) and numerous other publications.

In one configuration, for example, sample suspected of containing analyte is incubating with a monomer-/analyte conjugate and a reporter/reactant conjugate. In this case, the reactant is typically an antibody to the analyte. If the analyte is itself an antibody, the reactant can be a second antibody to the first antibody or it can be the antigen to the first antibody. Analyte present in sample and monomer/analyte conjugate compete for a limited amount of reporter/reactant. Polymerization-induced separation of free from specifically-bound reporter/reactant enables the detection and measurement of analyte initially present in the sample. This configuration is referred to as competitive.

In the competitive configuration, the immunoassays of this invention can be used to measure both monoepitopic compounds (haptens) and multiepitopic compounds. Multiepitopic is meant to include both compounds having more than one unique epitope. Maximum sensitivity is generally attained when the reactant is monovalent with respect to the analyte.

In another configuration, the immunoassays of this invention can be performed as sandwich immunoassays. This configuration is appropriate only for multiepitopic analytes. In the forward sandwich configuration, excess monomer/reactant conjugate is incubated with sample suspected of containing analyte. In this case, the reactant is typically an antibody to the analyte. If the analyte is itself an antibody, the reactant in the reporter/reactant conjugate can be either a second antibody to the first antibody or an antigen to the first antibody. Incubation is carried out under conditions in which specific binding is expected to occur. Following polymerization of monomer/reactant, excess reporter/reactant conjugate is added to the immunoassay mixture. Typically, the reactant is an antibody which binds to a different epitope from that to which the monomer/reactant conjugate binds. Again, if the analyte is itself an antibody, the reactant in the reporter/reactant conjugate can be either an antibody to the first antibody or an antigen to the first antibody. After an appropriate incubation to allow specific binding to occur, the presence or amount of reporter/reactant specifically bound to the polymer is determined. The polymer particles can be washed if desired to remove any free reporter/reactant. In general, however, it is thought sufficient to simply dilute the reaction mixture 2 to 100-fold prior to measuring the amount of reporter associated with the polymer particle. Similarly, if desired, the polymer particles can be separated from solution and the reporter associated with them eluted prior to detection or measurement.

The order of addition of reagents can also be reversed, i.e., sample suspected of containing analyte can be incubated with reporter/reactant prior to addition of monomer/reactant conjugage. This configuration is referred to as a reverse sandwich immunoassay. Likewise, sample, reporter/reactant, and monomer/reactant conjugate can be incubated simultaneously rather than sequentially, in which case the immunoassay is referred to as a simultaneous sandwich immunoassay. Of the three possible sandwich configurations, the simultaneous sandwich immunoassay is most preferred because it requires the least number of manipulations. All three configurations, however, offer significant advantages over prior art sandwich immunoassays in that incubation times are shortened and washing steps are eliminated.

In another configuration, the immunoassays of this invention can be performed by incubating patient sample suspected of containing analyte with monomer/-reactant conjugate (the reactant being an antibody to the analyte) under conditions where specific binding is expected to occur. Reporter/reactant can be added sequentially or simultaneously but in this case the reactant is an antibody to the monomer/reactant-analyte complex rather than to the analyte. Following polymerization-induced separation of free from specifically-bound reporter/reactant, the presence or amount of reporter/reactant specifically bound to the polymer particles is determined. In this configuration, the first reactant (anti-analyte) can be conjugated to either monomer or reporter. Likewise, the second reactant (anti-first reactant-analyte complex) can be conjugated to either monomer or reporter, whichever was not conjugated to the first reactant. This configuration, which is referred to as noncompetitive, offers the advantage that both reactants can be employed in excess. Thus, the sensitivity of the immunoassay is not strictly limited by the affinity constants of the reactants. This configuration is also appropriate for both monoepitopic and multiepitopic analytes.

Where it is of interest to determine the presence of two or more analytes in a sample simultaneously, multiple reporter/reactant conjugates can be employed in any of the above configurations, each reporter producing a detectably different signal from every other reporter. For example, the presence of two viruses in a single sample, such as lymphodenopathy-associated virus (LAV) and hepatitis B virus can be determined by employing antibodies to each of the viruses, one conjugated with fluorescein and the other with a phycobiliprotein. The simultaneous measurement of two or more analytes in the same sample could also be of interest in therapeutic drug monitoring, where drugs are co-administered, and in the monitoring of serum proteins, such as the immunoglobulins, and hormones, for example, in thyroid function testing.

The immunoassays of this invention utilize a monomer/reactant conjugate. Typically, the reactant is an antibody or an antigen. However, other reactants are known in the art, including e.g., lectins, receptors, transport proteins, and Staphylococcal protein A. Where the reactant is an antibody, either monoclonal or polyclonal antibodies can be used. Prior to conjugation, the antibody will in general be at least partially purified by methods known in the art.

The monomer is typically an ethylenically or acetylenically unsaturated compound containing at least one functionality for coupling to the reactant. Functionalities in the reactant can include, for example, covalently bondable functionalities such as hydroxyl, amine, carboxy, or sulfhydryl. Olefinically unsaturated monomers can be selected from compounds having the general formula:

$$\begin{array}{c} R_4 \\ \diagdown \\ \diagup \\ R_3 \end{array} C=C \begin{array}{c} R_1 \\ \diagup \\ \diagdown \\ R_2 \end{array}$$

where $R_1$ is H or a lower alkyl radical having from one to eight carbon atoms and $R_2$ can be:

—H
—COCl
—COOH
—$CO_2(CH_2)_nOH$ (n=1-8)
—$CH_2NH_2$
—$CH_2Cl$
—$CO_2C_2H_4NHR$ (R=H or any organic group)

$$-CO_2CH_2-CH\underset{O}{\overset{}{\diagdown\diagup}}CH_2$$

—$CO_2CH_2CHOHCH_2OH$
—CHO

—⟨phenyl⟩—$CH_2Cl$

—$CO_2(CH_2)nNCO$ (n=1-8)

—⟨phenyl⟩—NCO    —⟨phenyl⟩—NCS $R_3$ and $R_4$ are most usually H, however, they can be chosen to provide an unsaturated group, e.g. any allyl monomer:
$CH_2=CH-CH_2-$
a vinylene monomer:
—CH=CH—
or a diene monomer:

$$\begin{array}{c} \diagdown \\ \diagup \end{array} C=C-C=C \begin{array}{c} \diagup \\ \diagdown \end{array}$$

Alternatively, $R_2$ and $R_3$ can be combined as, e.g.,
—CO—O—CO—
to form $$\begin{array}{c} R_4 \\ \diagdown \\ \\ OC \end{array} C=C \begin{array}{c} R_1 \\ \diagup \\ \\ CO \end{array} \\ \diagdown O \diagup$$

Also, acetylenically unsaturated monomers having a reactable group are also useful.
—C≡C—

In addition, polyunsaturated molecules, oligomers or polymers (generally with defined unsaturation) having reactable groups will be useful. For representative examples see: Hoffman, A. S., "Electron Curing of Coatings", Isotopes and Radiation Technology, 9:1, pp. 78–92 (1971).

Specific monomers which can be used include acrylic acid, methacrylic acid, acryloyl chloride, methacryloyl chloride, glycidyl acrylate or methacrylate, glycerol acrylate or methacrylate, allylamine, allyl chloride, hydroxy-lower alkyl-acrylates (e.g., 2-hydroxyethyl methacrylate (HEMA) or 3-hydroxypropyl methacrylate), and amino lower alkyl-acrylates (e.g., 2-aminoethylmethacrylate), and vinyl benzoate.

Preferred monomers are those which are soluble in water or water/polar organic solvent mixtures.

Covalent coupling of the monomer to the reactant or its attached carbohydrate (in the case of glycoprotein reactants) can be carried out by any number of known chemical methods. For example, the monomer and/or the reactant can be activated to produce a stable but chemically reactive intermediate which can be subsequently reacted. The reactant can also be activated by periodate oxidation of the attached carbohydrates, if the reactant is a glycoprotein. This reaction forms aldehydes which can then condense with amino groups on the monomers, such as 2-aminoethyl methacrylate, to form a Schiff base. This Schiff base can be reduced with sodium cyanoborohydride to form a stable covaltn linkage. The monomer in the form of an acid halide may also be directly reacted with the reactant in the presence of an acid scavenger to remove acid as it is formed during the reaction. Additionally, bifunctional or hetero-bifunctional reagents may be used. Such bifunctional or hetero-bifunctional reagents are known and can be obtained, for example, from Pierce Chemical Company, Rockford, Ill. In almost all cases, the reaction conditions, i.e., time, temperature, solvent and pH, should be such as to avoid denaturation and/or degradation of the reactant. The monomer can be conjugated directly to the reactant or via a spacer arm.

Generally a single species of monomer will be conjugated to a selected reactant or analyte. However, it will be appreciated that a mixture of copolymerizable monomers can be conjugated to the reactant or analyte and which are thereafter separated by polymerization.

Homopolymerization of the monomer/reactant conjugate with itself or copolymerization with nonderivatized monomers is initiated by generation of free radicals. Nonderivatized monomers which may be used include, for example, ethylenically and/or acetylenically unsaturated monomers, as previously discussed, alkyl acrylates or methacrylates where the alkyl radical contains from 1 to 8 carbons, acrylonitrile and vinyl acetate. Also, cross-linking compounds may be copolymerized with the monomer/reactant conjugate. Such cross-linking compounds may include, for example, N,N'-methylenebisacrylamide or a di-, tri-or tetramethacrylate or acrylate. The percentage of derivatized and nonderivatized monomer may vary from traces up to 100%, but the preferable range is between 0.001 to 100% derivatized monomer and 0 to 99.999% nonderivatized monomer.

In addition to a monomer/reactant conjugate, a reporter/reactant conjugate is also required. The reporter can be chosen from any of those known in the art, including enzymes, fluorophores, radioisotopes, chemiluminescent materials, dye particles, etc. In general, however, fluorophores are preferred. Some suitable fluorophores include fluorescein, rhodamine, phycoerythrin, and Nile blue.

Methods of coupling the reporter to the reactant or analyte are well-known in the art. In general, covalent coupling is preferred, although other means of attachment are possible. The reactive sites which can be utilized for attachment are the same as those discussed above. In general, it is desirable to label the reactant with reporter as heavily as possible without loss of binding activity.

Separation of the specifically bound from the free reactants is accomplished by polymerization of the monomer/reactant conjugate. Polymerization or copolymerization with nonderivatized monomer is generally conducted at about room temperature with or without agitation. A surface active agent (e.g., detergent) may or may not be present. Although the reaction may be carried out in the presence of oxygen, it is generally preferred to conduct the reaction in the absence of oxygen or in the presence of a controlled amount of oxygen. The pH range may vary widely from pH 3 to pH 10, although it is preferable to select a pH where the reactant remains the most stable, which is typically between pH 6 and 8. If a surface active agent is used, suitable compounds, such as sodium dodecyl sulfate, sodium stearate, or nonionic materials such as polyethyleneoxide lauryl ether, may be employed.

The free radicals may be generated by oxidation-reduction initiation, photochemical initiation, ionizing radiation or thermal initiation. An advantage of both oxidation-reduction initiation and photochemical initiation is production of free radicals at reasonable rates at relatively low temperature (22°-37° C.). Types of oxidation-reduction initiators which may be used include (1) peroxides in combination with a reducing agent, e.g., hydrogen peroxide with ferrous ion, benzoyl peroxide with N,N-dialkylaniline or toluidine, and (2) persulfates in combination with a reducing agent such as N,N,N',N'-tetraethylmethylenediamine (TEMED), sodium metabisulfite or sodium thiosulfate. Specifically, ammonium persulfate, benzoyl peroxide, lauryl peroxide, t-butyl hydroperoxide, t-butyl perbenzoate, cumene hydroperoxide, or mixtures thereof with reducing agents, such as sodium bisulfite or sodium thiosulfate, may be used. It also appears that sodium bisulfite alone may be used for polymerization.

Photoinitiated polymerization may also be used by employing photoinitiators, such as azodiisobutyronitrile, azodiisobutyroamide, benzoin methyl ether, riboflavin, thiazine dye such as methylene blue and eosin, and transition metals such as ferric chloride or diazidotetraamminecobalt (III) azide, in combination with ultraviolet and/or visible light irradiation of the reaction system.

Ionizing radiation may also be employed utilizing radiation from a radioactive source or a particle accelerator.

Polymerization can be carried out in the presence of various physiological materials commonly encountered in biological fluids.

Nonderivatized monomers and polymerization initiating compounds can be present in the reaction mixture throughout the immunoassay or they can be added at any appropriate time. Measurement of the amount of reporter specifically bound to the polymer can be made in any of several ways depending upon the type of signal provided by the reporter. In one embodiment, the reporter is a fluorophore and fluorescence associated with polymer particles is detected or measured by flow microfluorimetry. In another embodiment, fluorescence associated with polymer particles is measured after filtration of the particles.

The following examples are provided by way of illustration, rather than implying any limitation of the present invention.

EXPERIMENTAL

Examples presented here utilize a representative monomer (2-hydroxyethyl methacrylate, HEMA), two antibodies and an antigen (human IgM) to be detected. The first antibody is a mouse monoclonal designated 2H1, which reacts with the kappa light chain of human IgM and is conjugated with monomer. The second antibody is a mouse monoclonal designated 2C3, which reacts with the mu heavy chain of human IgM and does not interfere with the binding of the first antibody to human IgM. The second antibody is labeled with a fluorescent tag. Briefly stated, these examples utilize a simultaneous sandwich immunoassay configuration in which the presence of the analyte to be detected mediates the incorporation of reporter/reactant (fluorescein labeled 2C3 antibody) into the polymer formed. The amount of reporter/reactant specifically bound to the polymer, i.e. the fluorescence intensity, is proportional to the amount of analyte in the sample. In a typical protocol, the two reactant conjugates are incubated together with the sample suspected of containing analyte to form a ternary complex. Nonderivatized (free) monomer is then added, and subsequent initiation of polymerization results in a copolymerization of nonderivatized monomer with monomer/reactant conjugate present in the ternary complex to form a fluorescent polymer. In the absence of analyte, the reporter/reactant conjugate does not form a ternary complex and the polymer particles are not substantially fluorescent.

Example 1 demonstrates (a) the activation of an acrylic monomer to allow its conjugation to the first reactant, (b) the conjugation of the acrylic monomer to the first reactant including evidence that the conjugation was successful, (c) the demonstration that the monomer/reactant conjugage retained the ability to bind to analyte, and (d) the conjugation of the second reactant with the reporter, fluorescein isothiocyanate. Example II demonstrates the polymerization of HEMA monomer in a buffered saline solution. In order to assure noninterference in this polymerization process by compounds commonly found in or added to biological samples, this reaction was also conducted in the presence of a sample of serum and in the presence of a nonionic detergent. Example III demonstrates an analyte-mediated incorporation of fluorescence into the insoluble polymer particles. This was accomplished by first incubating samples of the monomer/reactant conjugate and the reporter/reactant conjugate either with analyte or with a control buffer solution. After subsequent polymerization the particles formed were analyzed by flow cytometry and the analyte positive sample was found to contain highly fluorescent particles, while the particles contained in the control solution exhibited only background fluorescence. Likewise the extent of this fluorescence incorporation into the particles was found to be directly related to the amount of analyte present, forming the basis for a quantitative immunoassay system.

Example IV illustrates the synthesis of a N-hydroxysuccinimide ester of the monomer vinyl benzoic acid and its conjugation to an antibody reactant. The resultant monomer/antibody conjugate is employed with a fluorescein antibody conjugate (the latter antibody being directed to a second noncompeting epitopic site) in a sandwich immunoassay, wherein the polymer particles formed by copolymerization of the monomer/antibody conjugate with free monomer are separated from the bulk solution by filtration through a 0.45 μm pore size cellulose acetate filter, washed and the signal associated therewith read from the filter using a front surface fluorimeter.

Example V illustrates a simultaneous two-color immunoassay for IgG and IgM. The same monomer/antibody conjugate is employed as in Example I with two reporter/reactant conjugates, one specific for IgG and conjugated to phycoerythrin and one specific for IgM and conjugated to fluorescein. Measurement of particle-associated red and green fluorescence is made on a flow microfluorimeter.

EXAMPLE I

A: Synthesis of an Activated Acrylic Acid Monomer for Conjugation to Reactant A mixture containing N-hydroxysuccinimide (NHS) (4.6 g, 40 mmol) and acryloyl chloride (18 mL, 220 mmol) was refluxed with vigorous stirring for 3 hours in an anhydrous atmosphere and the reaction mixture, a homogeneous solution, was evaporated to a syrup. Distilled water (50 mL) was added to the syrup and the mixture was stirred for 30 minutes at 4° C. Upon addition of chloroform (50 mL), the mixture was separated into layers, and the organic layer was extracted successively with water (generally 5 times with 50 mL each time) until the pH of the water layer was approximately 5. The aqueous solutions so obtained were combined and extracted once with chloroform (50 mL); this chloroform solution and the chloroform solution from above were combined, dried over sodium sulfate, and evaporated to a syrup overnight at −20° C., were triturated with diethyl ether, and harvested by filtration.

Recrystallization from absolute ethanol yielded 2.0 g of the desired product. This compound was analyzed by mass spectrometry, infrared spectroscopy, NMR, liquid chromatography, and melting point, and proved to be the N-hydroxysuccinimide ester of acrylic acid (FIG. 1a).

B: Preparation of a Monomer/Reactant Conjugate

The N-hydroxysuccinimide ester of acrylic acid (NSA) was reacted with mouse monoclonal antibody (MAb) 2H1 as follows: 2.2 mg MAb in 0.29M sodium carbonate buffer, pH 9.3, was added to 20 micrograms of NSA in a total volume of 0.5 mL. The reaction mixture was incubated at 37° C. for one hour with constant stirring. Of this solution, 100 microliters was then taken for an analysis by reversed-phase high-performance liquid chromatography (RP-HPLC), which revealed the amount of free acrylic acid (arising from nonspecific hydrolysis of NSA) and remaining NSA in the reaction mix (Table 1) (FIG. 1b).

TABLE 1

| RESULTS OF HPLC ANALYSIS OF MONOMER CONJUGATION REACTION MIXTURE | | | |
|---|---|---|---|
| | Antibody | NSA (Activated) (monomer) | Acrylic Acid |
| Amount added, nanomoles | 14.5 | 116.0 | 0.0 |
| Amount detected in solution, nanomoles | Not determined | 0.0 | 26.7 |

This indicated that a net of 89 nanomoles of monomer was attached to the 14.5 nanomoles of MAb for a ratio of 6.2 monomer molecules per MAb.

To remove residula NSA and its hydrolysis products and for further characterization of the derivatized antibody, 200 microliters of the reaction mixture was chromatographed on a column of Sephadex ® G-25 (beads of dextran cross-linked with epichlorohydrin from Pharmacia Fine Chemicals AB, Uppsala, Sweden) in the same carbonate buffer to which bovine serum albumin, 0.1 mg/mL, was added to prevent nonspecific adsorption of polypeptides to the Sephadex ® G-25.

A sample of the monomer/reactant conjugate was then analyzed by isoelectric focusing. In this procedure, the polypeptide subunits of the proteins were separated according to their isoelectric point, or pH at which they had no net positive or negative charge. For this purpose, the heavy and light chains of the monomer/reactant conjugate were first dissociated in the presence of 3% (w/v) sodium dodecyl sulfate (SDS) and 5% (v/v) 2-mercaptoethanol and separated on the basis of molecular weight by electrophoresis in an SDS-polyacrylamide slab gel. The separated heavy and light chains of the reactant were cut out from the gel and analyzed further by isoelectric focusing in a polyacrylamide slab gel according to their isoelectric point. Staining of the isoelectric focusing gel with dye (Coomassie Brilliant Blue R-250) provided a characteristic pattern of bands for each sample. Since both the heavy and light chains of antibodies are glycoproteins which contain intrinsic variations in their sialic acid content, each heavy and light chain can be separated by a charge into a characteristic family of bands, with each band containing a polypeptide and differing amounts of sialic acid. As the reaction of the activated acrylic acid occurred primarily with amino functional groups on protein lysine residues, the addition of monomer to MAb would be expected to neutralize one positive charge on the protein subunit for each molecule of acrylic acid attached. This in turn would be expected to change the isoelectric point of the derivatized protein.

Figure 2:
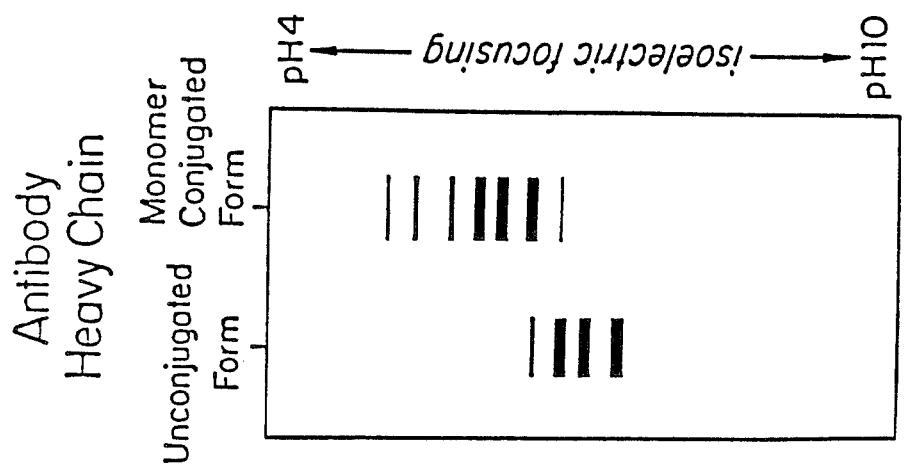
FIG. 2 is a diagrammatic representation of a polyacrylamide isoelectric focusing gel of the heavy chain of antibody reactant 2Hl before and after conjugation with acrylic acid.

The results of the isoelectric focusing analysis indicated that each heavy chain was modified by the covalent attachment of approximately three acrylic monomers (FIG. 2). Analysis also indicated that the electrophoretic pattern of monomer-derivatized light chain was so close to the nonderivatized polypeptide pattern that essentially minimal conjugation of monomer to light chains had occurred. On this basis, it was estimated that six moles of acrylic acid monomer was conjugated to each mole of antibody (3 per heavy chain times 2 heavy chains per antibody), which was in agreement with the analysis by RP-HPLC.

C: Demonstration that the Monomer/Reactant Conjugate Retained Binding Capacity for Analyte To show that the purified monomer/reactant conjugate was still active, it was tested in an enzyme linked immmunosorbent assay (ELISA), and the results indicated no loss of specific binding capacity. For this purpose, human IgG (which contain the same kappa chain antigen as human IgM) was absorbed to the surfaces of wells in a micro ELISA plate (96 wells). The wells were washed, residual nonspecific adsorbing sites on the plastic surface were blocked with bovine serum albumin, and then incubated with serial dilutions of the antibodies (control antibody and monomer/antibody conjugate). The plate was again washed, incubated with goat anti-mouse immunoglobulin conjugated to horseradish peroxidase, 0-phenylenediamine and hydrogen peroxide. Dilute aqueous sulfuric acid was added to stop the reaction, the plates were assayed on a micro ELISA reader, and the optical densities of each dilution of monomer/antibody conjugate compared with that of the control antibody. On a molar basis, the monomer/reactant conjugate demonstrated comparable specific binding activity to the nonconjugated antibody alone.

D: Preparation of a Reporter/Reactant Conjugate

The final step in the assembly of the components of a simultaneous sandwich immunoasssy system was the identification of a second antibody (2C3, which reacts with the mu heavy chain of human IgM) that bound to a different epitope of the analyte, thus it did not block the binding of the first, monomer/reactant conjugate to the analyte. The second antibody reactant was labeled with a reporter (fluorescein). For this purpose, 60 micrograms (20 microliters of a 3.0 mg/mL solution in DMSO) of fluorescein isothiocyanate isomer II (FITC) was added to 1 milligram of antibody 2C3 in 0.125 mL of 0.27M carbonate buffer, pH 9.3. The mixture was incubated for 30 minutes at 37° C. and chromatographed on a column of Sephadex ® G-25 in phosphate buffered saline to which 0.5M NaCl and 0.1% NaN₃ had been added. This separated the fluorescein labeled antibody from any free FITC that remained in solution. The peak was collected in a volume of 0.25 ml and the fluorescein-to-antibody ratio, calculated from the absorbences at 280 nm and 495 nm using the equation F/Ab ratio=$3.1 \times A495/A280 - 0.31 \times A495$, was found to be 4.7. Using methods similar to those in Example I.C, this reporter/reactant was found to be fully capable of specifically binding to analyte.

EXAMPLE II

Polymerization of Hema Monomer in a Buffered Saline Solution

Figure 3:
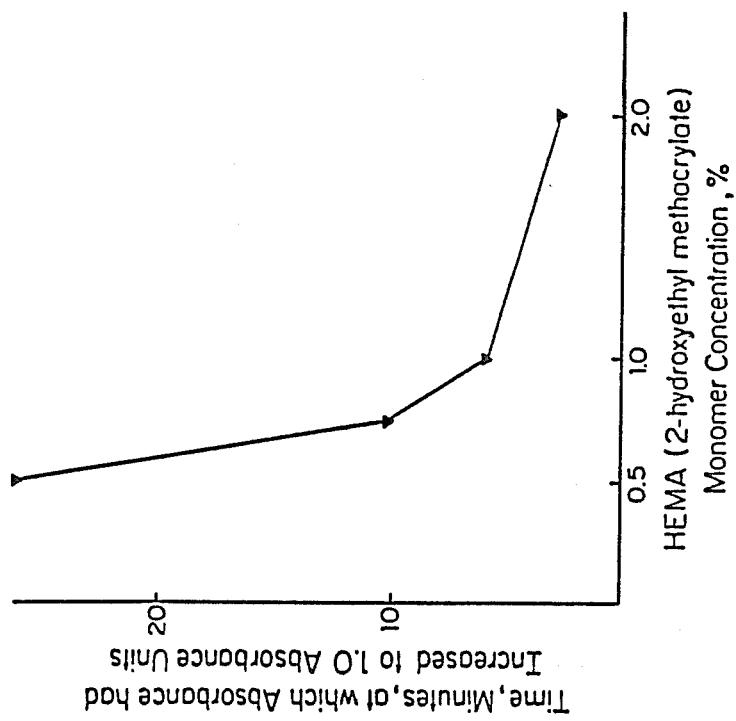
FIG. 3 depicts the effect of monomer 2-hydroxyethylmethacylate (HEMA) concentration of the rate of formation of insoluble HEMA homopolymer particles.

Polymerization of 2-hydroxyethyl methacrylate in the presence of physiological compounds was carried out as follows: to 2.73 mL of distilled water or phosphate-buffered saline, pH 7.4, was added 0.06 to 0.24 mL of 25% (v/v) 2-hydroxyethyl methacrylate (HEMA, Aldrich Chemical Company). Water was added to a final volume of 2.97 mL, as necessary. After bubbling prepurified nitrogen through a Pasteur pipette into the bottom of the cuvette for at least five minutes, 30 microliters of 1M $Na_2S_2O_5$ was added and the precipitation of the resulting polymer was followed at 550 nm with a Beckman Model 26 spectrophotometer. FIG. 3 illustrates the dependence of the rate of precipitation on the concentration of monomer. From this data, a concentration of 2% was chosen.

Inclusion of fetal calf serum, up to 10% (v/v), or "Nonidet P-40", a nonionic detergent, available from Shell Chemical Co., at concentrations up to 1% (w/v), had no effect on the rate of formation of the polymer particles. Since fetal calf serum contains a variety of proteins and other physiological compounds, this indicates that most proteins and physiological compounds will not inhibit formation of the polymer particles. Since nonionic detergents are commonly used in immunoassays to solubilize biological substances, this indicates that it will be possible to utilize detergents in polymerization-induced separation immunoassays without interference.

EXAMPLE III

Demonstration of Analyte-Specific Incorporation of Fluorescence into Polymer

This example illustrates a simultaneous two antibody sandwich immunoassay method. In this method, the reporter/reactant (fluorescein-labeled 2C3, 5 micrograms), the analyte (human IgM 4.5 micrograms) and the monomer/reactant (acrylic acid-labeled 2H1, 5 micrograms) were incubated together, which resulted in the formation of a ternary complex or sandwich containing both monomer and reporter. Copolymerization of this complex with additional nonderivatized monomer (HEMA) resulted in the formation of fluorescent, polymer particles (sample a).

For comparison, a control sample was prepared that was identical to the first except the analyte was omitted. This resulted in the formation of polymer particles that contained monomer/reactant but not reporter/reactant, hence the polymer particles were nonfluorescent (sample b). To quantitatively compare the amounts of incorporation of fluorescence into the polymer particles from the two samples, they were subjected to quantitative flow analysis using a flow cytometer.

After the polymerization had proceeded for ten minutes, the suspension of polymer particles was diluted one-hundred-fold and then introduced into a flow cytometer (Becton Dickinson, FACS IV) equipped with an Argon ion laser light source. In this procedure, the suspended particles were carried single-file in a laminar stream of buffer. Interrogation of the particle stream with the laser beam generated light scatter each time a particle entered the laser pathway. The extent of the light scatter was a reflection of particle size and shape. The measurement of light scatter is used to electronically trigger a simultaneous measure of fluorescence emitted from the particle. In this way, fluorescence specifically associated with polymer particles can be selectively measured.

Figure 4:
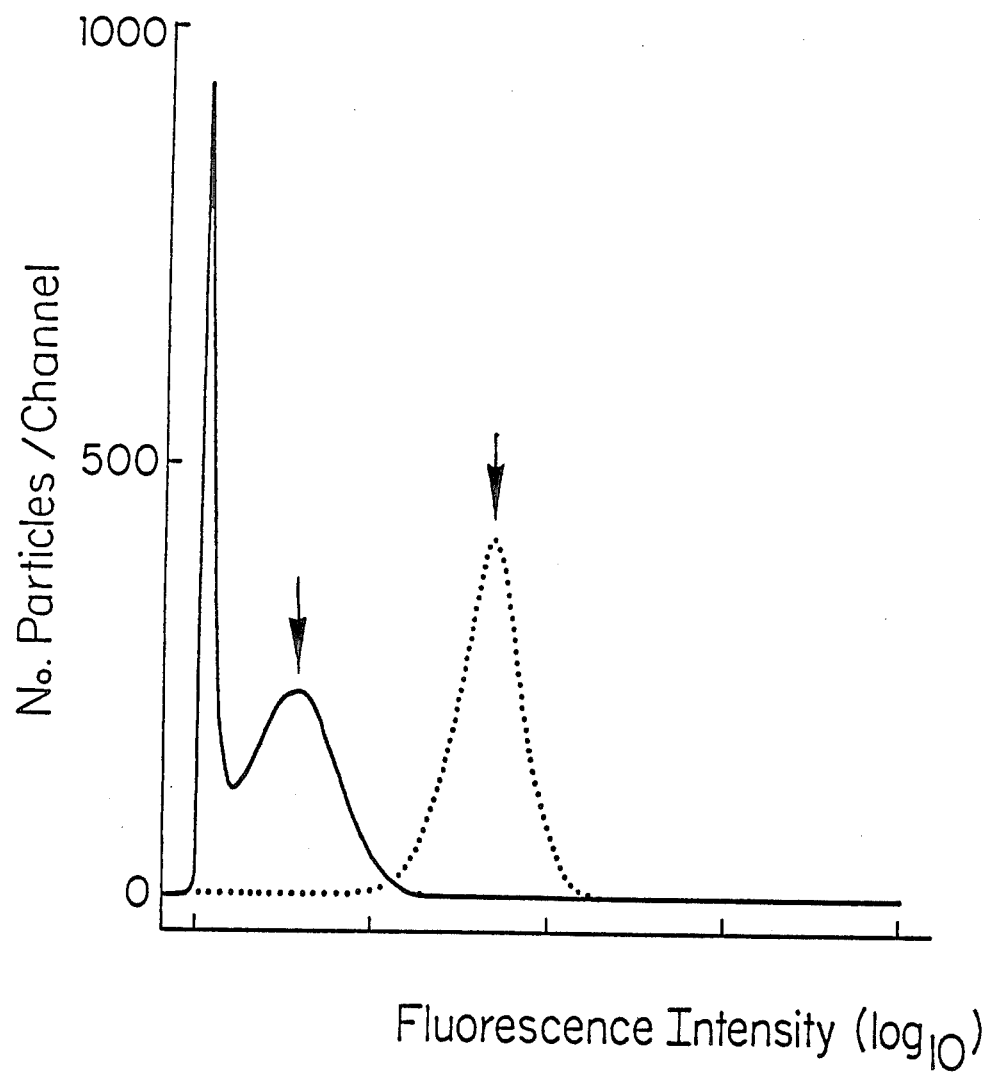
FIG. 4 depicts the incorporation of monomer/fluorescein tagged antibody reactant conjugates into reactant-containing polymer particles.
Figure 5:
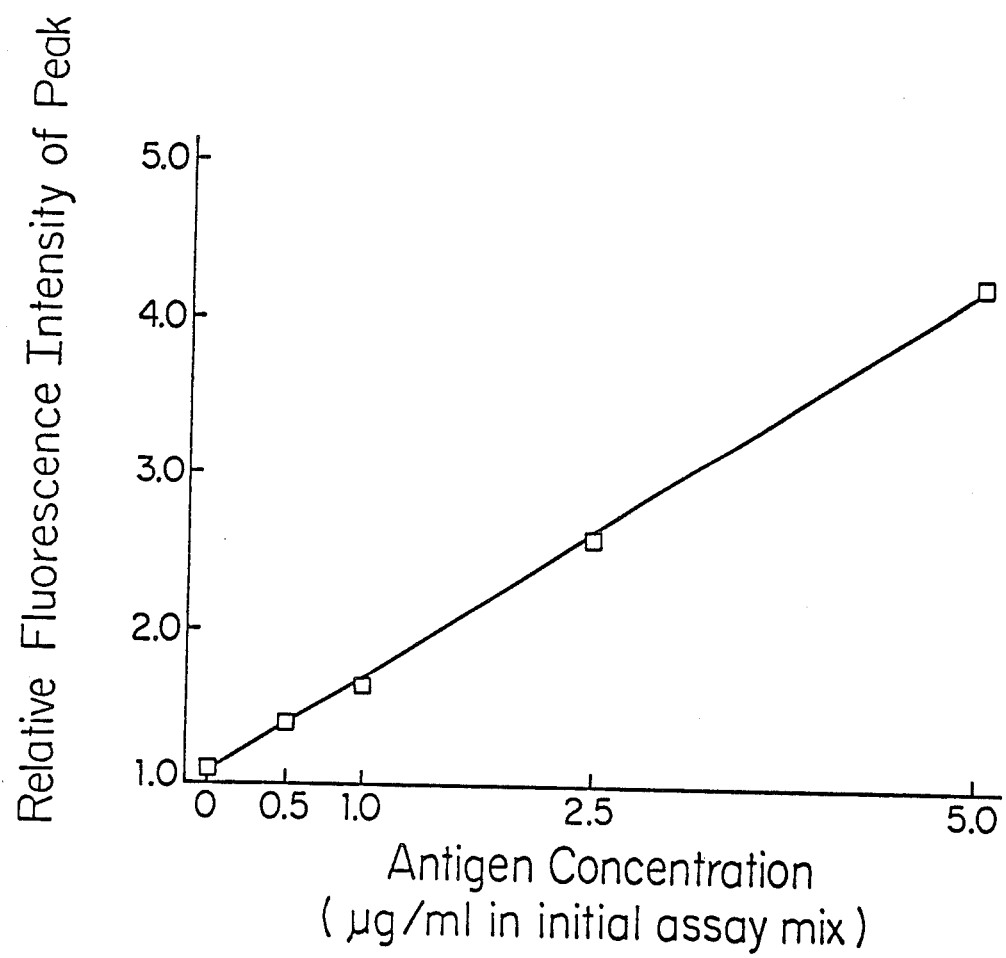
FIG. 5 is a diagram depicting the relationship between the fluorescence intensity and analyte concentration in one embodiment of the present invention.

The results are graphically presented in FIG. 4, which compares the fluorescence intensity of copolymer particles from a sample a (dotted line) with the fluorescence intensity of copolymer particles from a control sample b (solid line), from which the analyte was omitted. The fluorescence intensity of the copolymer particles formed in the presence of analyte (complete system) was shifted over 73 channels relative to the control (see arrows in FIG. 4). The fluoescence intensity scale (x axis) is logarithmic, and a shift of 73 channels corresponded to an 20-fold increase in fluorescence intensity. This increase in fluorescence intensity proved to be a linear function of the amount of analyte present in the sample. FIG. 5 is a plot of fluorescence intensity, on a linear scale, against the amount of analyte present in the sample, using 1 microgram of each reactant conjugate and otherwise the same conditions as used in FIG. 3.

EXAMPLE IV

A: Synthesis of the N-Hydroxysuccinimide (NHS) Ester of 4-Vinyl Benzoic Acid (VBA)

To 1 g (6.74 mmoles) of VBA in 40 ml of tetrahydrofuran (THF) were added 0.775 g of NHS and 1.39 g of dicyclohexyl (carbodiimide). The resultant mixture was stirred overnight at room temperature. The mixture was filtered and a small amount of p-methoxyphenol was added to the filtrate. The filtrate was then evaporated to dryness, yielding pale yellow crystals which were subsequently triturated with diethyl ether. The resultant solid was recrystallized once from methanol. Analysis by NMR, mass spectrometry, and infrared spectroscopy confirmed the identity of the compound as N-succinimidyloxy-(4-vinyl benzoate) (NSB).

B: Conjugation of NSB to Monoclonal Antibody

A murine monoclonal antibody designated 2HI, which is reactive with kappa light chains of human immunoglobulin, was conjugated to NSB to yield a monomer/antibody conjugate. Briefly, to 7 mg of purified 2H1 IgG in 1.23 mL of 0.29M carbonate buffer (pH 9.3) was added 113 g of NSB in 11.3 µg of NSB in 11.3 µL of THF. The mixture was stirred for 1 hour at 37° C. and then chromatographed on a Sephadex G-25 column (PD-10 disposable column from Pharmacia Fine Chemicals, Piscataway, N.J.) which had been equilibrated in phosphate buffered saline (PBS, pH 7.4). Fractions were collected and their absorbance at 280 nm determined. The peak fractions were pooled, divided into 100 µL aliquots, and stored frozen at −20° C. until needed.

C: Conjugation of Fluorescein Isothiocyanate (FITC) to Monoclonal Antibody

A murine monoclonal antibody, designated 3F6, which is reacted with gamma heavy chains of human immunoglobulin, was conjugated to FITC to yield a reporter/antibody conjugate. Briefly, 60 µg (20 µL of a 3.0 mg/mL solution in DMSO) of FITC isomer II was added to 1 mg of purified 3F6 IgG in 0.125 mL of 0.29M carbonate buffer (pH 9.3). The mixture was incubated for one-half hour at 37° C. and them chromatographed on a column of Sephadex ® G-25 equilibrated in PBS/0.5M NaCl/0.1% (w/v) NaN₃. Fractions were collected and the fluorescein-to-antibody protein (F/P) ratio of the peak fractions determined using the following equation:

$$F/P = (3.1 \times \frac{A_{495nm}}{A_{280nm}}) - (0.31 \times A_{495nm})$$

The F/P ratio was found to be approximately 5.

D: Polymerization-Induced Separation Immunoassay for Human IgG

An immunoassay for human IgG was performed using NSB-conjugated antibody 2H1 (Ab$_M$) and FITC-conjugated 3F6 (Ab$_F$). An IgG/kappa human myeloma protein was used as the antigen.

The assay was performed as follows: Ab$_M$ (30 µg/mL final concentration), Ab$_F$ (30 µg/mL final concentration), and hydroxyethylmethacrylate (HEMA, 1% (w/v) final concentration) were admixed with sample containing antigen in a total volume of 100 µL. After a ten minute incubation at 37° C., polymerization was initiated by the addition of 25 µL of 30 mM ammonium persulfate and 25 µL of 240 mM N,N,N'N'-tetraethylmethylenediamine (TEMED). Polymerization was conducted for twenty minutes at 37° C. The amount of fluorescence incorporated into the resultant copolymer particles was determined either by flow microfluorimetry or by filtration on a Screen Machine (Pandex Laboratories, Mundelein, Ill.). In the flow microfuorimetry method, a 50 µL aliquot of the reaction mixture was diluted into 2 mL of PBS prior to analysis on a FACS IV (Becton-Dickinson, Sunnyvale, Ca.). In the filtration method, a 50 µL aliquot of the reaction mixture was diluted with an equal volume of PBS containing 0.05% (w/v) Tween 20 and added to a well of a Screen Machine microtiter tray. The wells in these trays contain 0.45µ average pore size cellulose acetate filters. The filters were pre-equilibrated by washing with 1% (w/v) BSA in PBS.

Table I compares the relative fluorescence intensity obtained for various concentrations of antigen using the two methods of measurement.

TABLE I

| Antigen Concentration (µg/mL) | Relative Fluorescence Intensity | |
|---|---|---|
| | Flow Microfluorimetry | Filtration (× 10⁻²) |
| 0 | 2.9 | 11.7 |
| 0.007 | 4.0 | 12.9 |
| 0.015 | 4.7 | 13.4 |
| 0.03 | 5.8 | 17.5 |
| 0.06 | 9.0 | 25.0 |
| 0.125 | 16.0 | 37.2 |
| 0.250 | 27.2 | 64.0 |

EXAMPLE V

Polymerization-Induced Separation Immunoassay for the Simultaneous Two-Color Measurement of Human IgG and IgM NSB-conjugated 2H1 (Ab$_M$, to human kappa light chains) and FITC-conjugated 2C3 (AB$_F$, a murine monoclonal to human mu heavy chains) were prepared as described above.

A: Conjugation of R-Phycoerythrin to Monoclonal Antibody

The murine monoclonal antibody, designated 3F6, which is reactive with gamma heavy chains of human immunoglobulin, was conjugated to R-phycoerythrin (PE) to yield a reporter/antibody conjugate. R-phycoerythrin was purified from the red alga *Porphyra yesoensis* as described by Oi et al., J. Cell Biol., 93:981, 1982. Conjugation occurred via sulfoether linkage, using succinimidyl 4-(N-maleimidomethyl)cyclohexane-1-carboxylate (SMCC) as a bifunctional cross-linking agent. Briefly, thiol groups were introduced onto the antibody using S-acetylmercaptosuccinic anhydride, while reactive maleimide groups were introduced onto PE using SMCC. The PE derivative was then coupled to the antibody derivative.

The introduction of thiol groups into 3F6 was accomplished as follows: To 2.5 mg of purified 3F6 IgG in 0.5 mL of PBS was added 5 µl of a 60 mg/mL solution of S-acetylmercaptosuccinic anhydride in DMF. The mixture was incubated at room temperature with continuous stirring for one-half hour, after which 0.5 mL of 1M hydroxylamine, pH 7.0 and 0.05 mL of 0.1M Tris buffer, pH 7.0, containing 0.2M EDTA were added.

Incubation was continued for ten minutes at room temperature, after which the reaction mixture was chromatographed on a Sephadex G-25 column (1.0×45 cm) equilibrated in 0.02M phosphate buffer, pH 6.0, containing 0.005M EDTA. Fractions were collected and their absorbance at 280 nm determined. The peak fractions were pooled and the number of thiol groups per mole of IgG determined according to the method of Grassetti, et al., Arch. Biochem. Biophys. 119:41, 1967. Approximately seven thiols were introduced per mole of IgG.

Reactive maleimide groups were introduced into PE as follows: To 1.0 mg of PE in 1.0 mL of PBS was added 25 µL of a 0.9 mg/mL solution of SMCC in DMF. The mixture was incubated at room temperature for one-half hour, after which it was chromatographed on a Sephadex G-25 column (1.0×45 cm) equilibrated in 0.1M phosphate buffer, pH 6.5. Fractions were collected and their absorbance at 280 nm monitored. The peak fractions were pooled and the molar ratio of SMCC to PE determined according to the method of Ishikawa, J., Immunoassay 4:209, 1983. Approximately four molecules of SMCC were introduced per molecule of PE.

The resultant PE derivative was coupled to thiolated 3F6 as follows: To 1 mg of PE derivative in 2 mL of 0.1M phosphate buffer, pH 6.5, was added 1.5 mg of thiolated 3F6 in 1 mL of 0.02M phosphate buffer, pH 6.0, containing 0.005M EDTA. After mixing, 0.3 mL of 10X PBS was added and the resultant mixture was incubated at room temperature for two hours. After incubation, 50 µL of 0.1M N-ethylmaleimide in DMF was added. Incubation was continued for 10 minutes, after which the reaction mixture was chromatographed on a Sephacryl S-300 column (1.5×120 cm) equilibrated in PBS containing 0.1% (w/v) azide. Two PE-containing peaks were obtained, the higher molecular weight peak corresponding to 3F6-conjugated PE and the lower molecular weight peak, to unconjugated PE. The fractions corresponding to the high molecular weight peak were pooled and found to have a molar ratio of 3F6 to PE of 1.5. This conjugate is referred to as $Ab_{PE}$.

B: Simultaneous Two-Color Immunoassay of Human IgG and IgM

A polymerization-induced separation immunoassay for the simultaneous two-color measurement of human IgG and IgM was conducted as follows: $Ab_m$ (30 g/mL final concentration), $Ab_F$ (45 µg/mL final concentration), $Ab_{PE}$ (30 µg/ml final concentration) were admixed with sample containing varying amounts of both antigens in a total volume of 100 µL. An IgG/kappa myeloma protein and an IgM/kappa myeloma protein were used as antigens. After a ten-minute incubation at 37° C., polymerization was initiated by the addition of 25 µL of 30 mM ammonium persulfate and 25 µL of 240 mM TEMED. After 20 minutes polymerization, a 50 µL aliquot of the reaction mixture was diluted into 2 mL of PBS for analysis by multiparameter flow microfluorimetry using a FACS IV. A 488 µm laser line was used for excitation. A 560 µm dichroic mirror (Becton-Dickinson) was used to split the emission wavelengths. Additionally, 580 µm longpass and 540 µm shortpass filters (Ditric Optics, Hudson, Ma.) were placed in front of the red (PE) and green (FITC) photomultiplier tubes, respectively. A compensator was used to correct any residual spillover of green and red signals.

Simultaneous two-color measurement of IgG and IgM in a series of samples and presentation of the data as number of particles (vertical axis) versus log green fluorescence and versus log red fluorescence on a 64×64 dot grid (with each 4.5 dots representing an approximate doubling of fluorescence) was carried out. A first fluorescence profile of copolymer particles was formed in the presence of 0 µg/mL IgM and 1 µg/mL IgG and fluoresced red with no green fluorescence above background. A second fluorescence profile of copolymer particles formed in the presence of 1 µg/mL IgM and 0 µg/mL IgG particles fluoresced green. A fluorescence profile obtained by mixing the copolymer particles formed in the first profile with those formed in the second profile resulted in two distinct peaks, a green peak with contains the IgM bearing particles and a red peak which contains the IgG bearing particles.

Fluorescence profiles of copolymer particles formed in the presence of a constant amount of IgG (1 µg/mL) and varying amounts of IgM (0 µg/mL final concentration, 0.125 µg/mL, 0.500 µg/mL, and 1.0 µg/mL, respectively were obtained). The copolymer particles formed emitted both green and red fluorescence in proportion to the amount of each antigen present in the sample.

Although the foregoing invention has been described in some detail by way of illustration and example for purposes of clarity of understanding, it will be obvious that certain changes and modifications may be practiced within the scope of the appended claims.

What is claimed is:

1. An immunoassay method for determining the presence of more than one analyte in a fluid sample suspected of containing one or more of said analytes, comprising:
   (a) combining said fluid sample with an addition monomer/analyte conjugate for each analyte being determined to form a fluid sample mixture;
   (b) combining said mixture with reporter/reactant conjugates specific for bonding to each analyte thought to be contained in said fluid sample mixture under conditions favorable for the formation of the reporter-labelled analyte complexes and reporter-labelled monomer/analyte complexes, each reporter/analyte conjugate providing a detectably different signal from every other reporter present in said fluid sample mixture;

(c) separating said reporter-labelled monomer-/analyte-conjugate complexes by initiating addition polymerization in said mixture; and (d) detecting the incorporation of each reporter into each said polymerized complex as a measure of the analytes present in the sample.

2. The immunoassay method of claim 1 wherein the reporters are selected from the group consisting of radioisotopes, enzymes, enzyme inhibitors, enzyme cofactors, luminescent materials, and chromophores.

3. The immunoassay method of claim 1, the monomer comprising a polymerizable, ethylenically unsaturated organic monomer selected from the group consisting of:

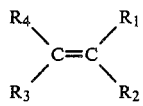

where $R_1$ is a hydrogen or lower alkyl having from 1 to 8 carbon atoms, $R_2$ is selected from the group consisting of:

—COCl
—COOH
$CO_2(CH_2)_n$ OH (n=1-8)
—$CH_2NH_2$
—$CH_2Cl$
$CO_2CH_2CH_2NHR$ (R=H or any organic group)

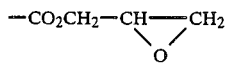

—$CO_2CH_2CHOHCH_2OH$
—CHO

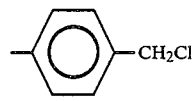

—$CO_2(CH_2)_n NCO$ (n=1-8)

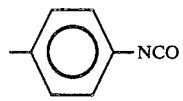 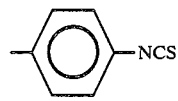

and $R_3$ and $R_4$ are selected from the group consisting of H and compounds which will provide a reactive ethylenically unsaturated group.

4. The immunoassay method of claim 3 wherein $R_3$ and $R_4$ are H.

5. The immunoassay method of claim 1, wherein said monomer comprises an acetylenically unsaturated reactive monomer having a functional group capable of forming a covalent bond with the reactant.

6. The immunoassay method of claim 1 wherein the monomer is 2-hydroxyethyl methacrylate.

7. The immunoassay method of claim 1 wherein the monomer is vinyl benzoate.

8. The immunoassay method of claim 1 wherein one reporter is fluorescein isothiocyanate.

9. The immunoassay method of claim 1 wherein one reporter is fluorescein and another is an R-phycoerythren.

10. The immunoassay method of claim 1 wherein the reactants and analytes are selected from the group consisting of antibodies, antigens and haptens.

11. The immunoassay method of claim 10 wherein one analyte is an immunoglobulin.

12. The immunoassay method of claim 11 wherein the immunoglobulin is IgM.

13. The immunoassay method of claim 12 wherein the IgM is from human-derived sources.

14. The immunoassay method of claim 1, further comprising detecting the incorporation of one reporter into the polymerized complex by flow cytometry.

15. The immunoassay method of claim 1, further comprising detecting the incorporation of reporter into the respective polymerized complexes by flow microfluorimetry and filtration.

* * * * *